(12) United States Patent
Petrescu (10) Patent No.: US 7,348,411 B2
(45) Date of Patent: Mar. 25, 2008

(54) PROCESS FOR MANUFACTURING FIBRIN MEMBRANES AND FIBRIN MEMBRANES OBTAINED ACCORDING TO THIS PROCESS

(76) Inventor: Dorin Olimpiu Petrescu, Viale Cassiodoro 4, 20145 Milano MI (IT)

( * ) Notice: Subject to any disclaimer, the term of this patent is extended or adjusted under 35 U.S.C. 154(b) by 223 days.

(21) Appl. No.: 10/536,612

(22) PCT Filed: Nov. 26, 2003

(86) PCT No.: PCT/IT03/00780

§ 371 (c)(1),
(2), (4) Date: May 25, 2005

(87) PCT Pub. No.: WO2004/048449

PCT Pub. Date: Jun. 10, 2004

(65) Prior Publication Data

US 2006/0088577 A1    Apr. 27, 2006

(30) Foreign Application Priority Data

Nov. 26, 2002  (IT) .......................... MI2002A2501

(51) Int. Cl.
*A61K 35/14* (2006.01)
*A61K 38/17* (2006.01)
*A61K 38/36* (2006.01)
*A61K 38/39* (2006.01)

(52) U.S. Cl. ..................... 530/380; 530/381; 530/382; 424/484; 424/529; 424/530

(58) Field of Classification Search .............. 424/484, 424/529, 530; 530/380, 381, 382
See application file for complete search history.

(56) References Cited

U.S. PATENT DOCUMENTS

| 4,427,651 A | * | 1/1984 | Stroetmann .................. 424/46 |
| 6,368,298 B1 | | 4/2002 | Beretta et al. |
| 2002/0131933 A1 | | 9/2002 | Delmotte |

FOREIGN PATENT DOCUMENTS

| JP | 52 156912 A | * | 12/1977 |
| WO | WO 98/58689 | * | 12/1998 |

* cited by examiner

*Primary Examiner*—Ruth A Davis
(74) *Attorney, Agent, or Firm*—Lucas & Mercanti, LLP (57) ABSTRACT

A process for manufacturing a fibrin membrane from blood plasma that was partially depleted and subjected to coagulation by adding a solution of a physiological coagulating agent, leaving the mixture to stay until forming a gelatinous blood clot, and then dehydrating said blood clot to obtain a fibrous membrane, which is subjected to washing with softening agents and then to drying until obtaining a flexible and mouldable membrane. The membrane so obtained is capable to provide an immediate and complete haemostasis, followed by a whole reabsorption, without risk of adhesions with the neighboring tissues, up to the cicatrisation of the injured tissue. The membrane is mouldable and elastic, and is provided with high mechanical properties. It may be soaked with disinfectant agents, drugs or tissue growth factors.

13 Claims, 9 Drawing Sheets

PROCESS FOR MANUFACTURING FIBRIN MEMBRANES AND FIBRIN MEMBRANES OBTAINED ACCORDING TO THIS PROCESS

This patent application claims the benefit of priority from Italian Patent Application No. MI2002A 002501 filed Nov. 26, 2002 through PCT Application Ser. No. PCT/IT03/000780 filed Nov. 26, 2003, the contents of each of which are incorporated herein by reference.

The present invention relates to the medical-surgical field, and in particular to a process for manufacturing fibrin membranes to be used as supports having high adhesiveness on human and animal tissues in cicatrisation and haemostasis processes, and a fibrin membrane obtained according to this process.

It is known that in medical-surgical applications, means for timely stopping haemorrhages, such as for example those due to external superficial wounds or lesions resulting from surgical operations, are of primary importance. It is necessary that said means are perfectly sterile and completely compatible with the organism whereon they will be applied. In the publication of J. Travis, "Buildings better bandages", Science News On Line, 1999, 155 (25):396, the need of new haemostatic means that are effective with respect to known dressings made with different kinds of fabrics (gauzes, bandages, etc.) is pointed out.

As a result of such needs, the idea of using fabrics or tissues soaked in high concentrations with natural proteins involved in blood coagulation was already developed, and has achieved first positive results. The use of a fibrin tissue provides an immediate and complete haemostasis, resulting in a whole reabsorption, without incurring adhesions with neighbouring tissues, thus causing the correct cicatrisation of the injured tissue. Nevertheless, the techniques so far used in manufacturing such haemostatic tissues are very expensive. A large-sized fibrin bandage can cost even more than one thousand dollars.

From the publication of C. Clark, "Dried polymerized fibrin sheets arrest bleeding", Tissue Engineering Weekly, Dec. 28, 1998, News Section, the use of liquid fibrin glue consisting of fibrinogen and thrombin is known, the utilization whereof is not free from disadvantages. The main disadvantage is the difficulty of intervention in certain surgical seats, wherein, in spite of using a specific device for their application, instances of overflowing happen prior to the fibrin solidification.

It is the object of the present invention to provide a process for manufacturing a fibrin membrane that overcomes said disadvantages. Such an object is achieved by a process, the main characteristics whereof are specified in Claim 1. Further characteristics of the process according to the present invention are specified in the subsequent claims, whereas the properties of the fibrin membrane are specified in claims 6-12.

A first remarkable advantage of the process according to the present invention is that of being quickly and simply feasible, thus providing concrete improvements, even from an economical point of view, with respect to the processes known in the art.

A second advantage of the present process derives from the properties of the membrane obtained according to said process, which membrane is completely compatible with the organism whereon it will be applied, being totally extracted from by-products of human or animal blood plasma.

Another advantage of the above-mentioned process resides in further properties of the resulting membrane, which shows high adhesiveness, capability of isolating a wound from external contaminant agents and of supporting the cicatrisation process in injured tissues.

A further advantage of the above-mentioned process consists in the possibility of packaging under sterile conditions the resulting membrane and preserving it in conditions of unchanged sterility until the time of use, that is until the direct application on the wounded tissue.

Further advantages and characteristics of the process according to the present invention and of the fibrin membrane obtained thereby will be clear to those skilled in the art from the following detailed description with reference to the annexed drawings, wherein.

The inventive idea on which the present invention is based is that of having surprisingly found that, by starting from blood plasma as it is or from depleted blood plasma, it is possible to easily and cheaply obtain wholly sterilizable fibrin membranes having physical and structural properties such as to make said membranes advantageously flexible, mouldable, strongly adhesive on human and animal tissues and soakable with different organic solutions, for example with disinfectant agents, cicatrising agents or drugs for controlled release formulations.

In the present description, by the term "depleted blood plasma" there is meant a by-product of haemoderivative industry, consisting of plasma remaining from extractions of various protein fractions, such as immunoglobulin, thrombin, antihaemophilic factor, albumin, etc.

The process for manufacturing said fibrin membrane according to the present invention includes the following operating steps:
a) adding a physiologic coagulant agent solution to depleted blood plasma, placed in suitable containers;
b) leaving the mixture to stay up to the formation of a gelatinous blood clot;
c) removing the transudate from said gelatinous blood clot until obtaining a fibrous membrane;
d) washing said fibrous membrane with dehydrating and softening agents;
e) exsiccating said fibrous membrane;
f) sterilizing said fibrous membrane.

In a preferred embodiment of the process according to the present invention, to depleted blood plasma, which was previously stabilized by a solution of an anticoagulant agent, such as sodium citrate, a solution of a clotting agent, such as calcium chloride, is added in an amount suitable to neutralize the amount of anticoagulant agent.

The so obtained mixture is directly poured into containers suitably sized to satisfy the requirements of use of the final membrane, leaving the whole to stay up to the formation of a gelatinous blood clot.

The transudate removing step, that is the removing of the supernatant containing plasmatic proteins, may include several steps in order to remove as much as possible any residues. For this purpose, substances such as inorganic salts (i.e. NaCl, $NaHCO_3$, and like), that are completely compatible with human and animal organisms can be used since they are already physiologically present therein. As a result of the transudate removing step, the blood clot takes the appearance of a fibrous membrane. This one is washed out several times with water and further treated in dehydrating and softening baths, using for example ethanol and propane-triol, in order to absorb even the last water traces.

Then the membrane is left to dry, for example in hot air flow, thereby obtaining a smooth, flexible, uniform, mouldable, elastic, semitransparent sheet withstanding moderate tensile stresses. The membrane thickness is a function of the layer thickness of plasma and clotting agent mixture, both being initially present in the container for forming the membrane.

The subsequent sterilization step of the dehydrated membrane that can be performed by means of methods known to those skilled in the art, is preferably carried out:

in an autoclave, for 20-30 min. at 120-122° C.; or according to the "STERRAD" method, using $H_2O_2$ for 60 min. at 45° C.; or by ionizing radiations.

In a preferred embodiment of the present invention, a gelatinous quadrangular shaped blood clot is obtained after addition of a calcium chloride solution to depleted blood plasma, being previously stabilized by sodium citrate. From such blood clot the transudate is removed by using NaCl, then washed 2-3 times with water and subsequently treated with ethanol and propane-triol. The resulting fibrin membrane is dried in hot air flow and sterilized in autoclave for 30 minutes at a temperature of 122° C.

The fibrin membrane obtained according to the above-mentioned process shows the physical properties given in the following operative examples of the invention. The characterization of said membrane is carried out in cooperation with Politecnico di Milano.

EXAMPLE 1

130 ml of depleted blood plasma and 10 ml of fresh blood plasma (supplied by Kedrion SpA, Castelvecchio Pascoli, LU, IT) were poured in a suitable rectangular container. An aqueous solution of $CaCl_2$ 2.6% p/v (using anhydrous $CaCl_2$, available on sale) was added at room temperature. Once formed, the blood clot was covered with NaCl powder (available on sale) in order to absorb the transudate and then washed with water. Last operation was repeated 2-3 times. The so obtained membrane was transferred into a bath of propane-triol 10% v/v in ethanol 95% (available on sale) and it was left to stay at room temperature for 16-24 hours.

The membrane was extracted, ethanol was evaporated in hot air flow. The membrane was inserted into a closed gas-permeable envelope (available on sale) and then such an envelope was placed in an autoclave for 25-30 minutes at 122° C. for sterilization.

EXAMPLE 2

The rectangular shaped sample A (52 mm×73 mm) was cut out from a human fibrin membrane obtained according to the above-mentioned process, sterilized in autoclave at 120° C. and stored at room temperature. In order to determine the physical properties regarded as critical for the clinical application, sample A was subjected to mechanical tensile and ultimate strength tests, as well as to morphological analysis at the electron microscope, having previously determined the thickness of the membrane.

The specimen thickness was measured by a millesimal micrometer Mitutoyo mod. 293-561-30, S/N 7083373, provided with a friction device allowing to impose high strains with good measurement reproducibility. To avoid damaging sample A, this one was inserted between two Teflon sheets, having measured thickness equal to 0.142 mm. From the final measurement, that of both Teflon sheets was then subtracted. To check the uniformity level of the considered membrane, thickness measurements were carried out in ten different points of the membrane spaced apart between them and from the edges by about 10 mm. The detected values were as follows:

| Sample | Mean thickness (μm) | Maximum thickness (μm) | Minimum thickness (μm) |
| --- | --- | --- | --- |
| A | 59 | 72 | 39 |

Tensile Tests

The mechanical properties of sample A were evaluated by monoaxial tensile tests using the equipment MTS Synergie 200 H S/N 261701/30 supplied by MTS (Minneapolis, Minn., USA), provided with a cell MTS S/N 2.1279, having 100N as an end-point. From the sample, two test-pieces were cut out using a template, and the thicknesses thereof were then measured at the barycentre of each test-piece by using the same millesimal micrometer previously used.

Each test-piece was subjected to the following process:
a) mechanical conditioning by performing of some loading and unloading cycles between 0 and 1.2N at a sliding crossbar speed corresponding to 20 mm/min.
b) breaking strength at a sliding crossbar speed corresponding to 20 mm/min.

Figure 1:
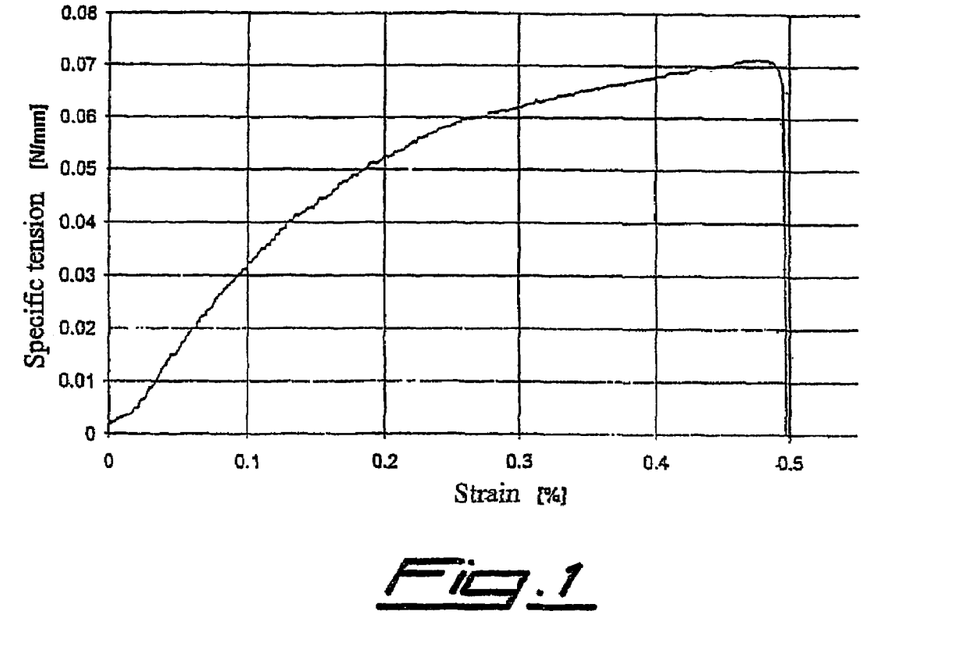
FIG. 1 shows the relationship between specific tension and strain in a specimen of sample A of fibrin membrane, subjected to tensile tests.
Figure 2:
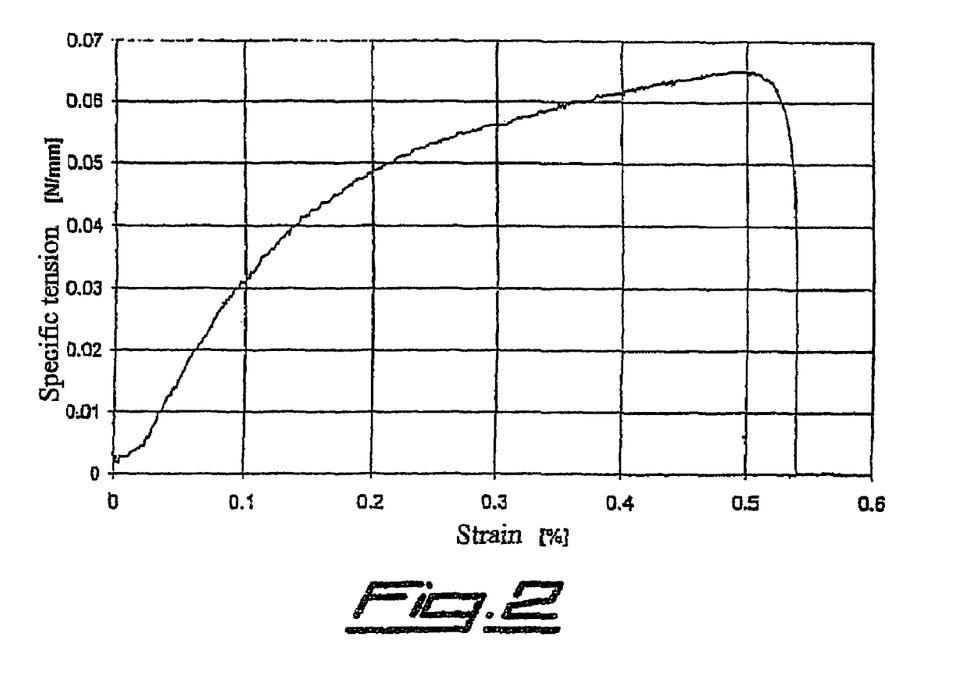
FIG. 2 shows the relationship between specific tension and strain in another specimen obtained from the same sample A, subjected to tensile tests.

The results of such tests, carried out at room temperature of 23±2° C., are represented in FIGS. 1 and 2 as a specific tension/strain ratio, whereas for a quantitative evaluation of both specimen properties the following data are given:

| Direction | Thickness (μm) | Modulus of elasticity K (N/mm) | Proportionality limit $T_P$ (N/mm) | Breaking limit $T_R$ (N/mm) |
| --- | --- | --- | --- | --- |
| 1 | 59 | 0.076 | 0.040 | 0.071 |
| 2 | 59 | 0.413 | 0.030 | 0.065 | where:

Direction denotes the axis along which the tensile strength was exerted: one time along the axis corresponding to the specimen length, another time along the axis corresponding to its width;

T (N/mm), or specific tension, denotes the ratio between the force applied to the specimen and its width unit (1 mm);

ε (%), or strain, means the percent ratio between the elongation undergone by the specimen and its starting length;

K (N/mm), or modulus of elasticity, means the ratio between a specific tension increase and a strain increase evaluated in the range between the values corresponding to 30% and 60% of proportionality limit;

$T_P$ (N/mm), or proportionality limit, means the limit value of tension, beyond which the tension/strain ratio is no more linear.

$T_R$ (N/mm), or breaking limit, the maximum value before breaking.

Figure 3:
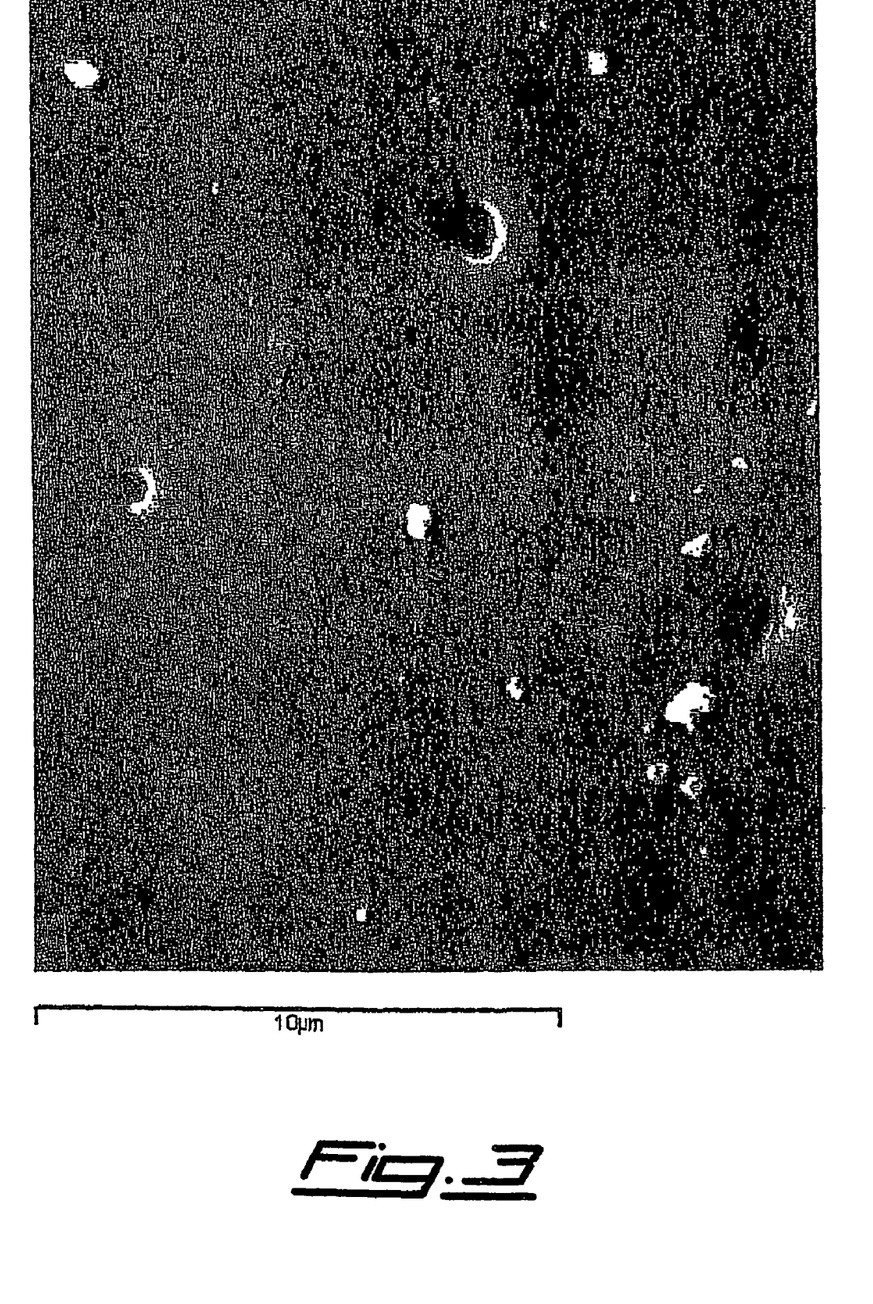
FIG. 3 shows an electron microscope image of said sample A.

Finally, sample A was observed at the electron microscope: the surface image thereof is shown in FIG. 3.

Figure 4:
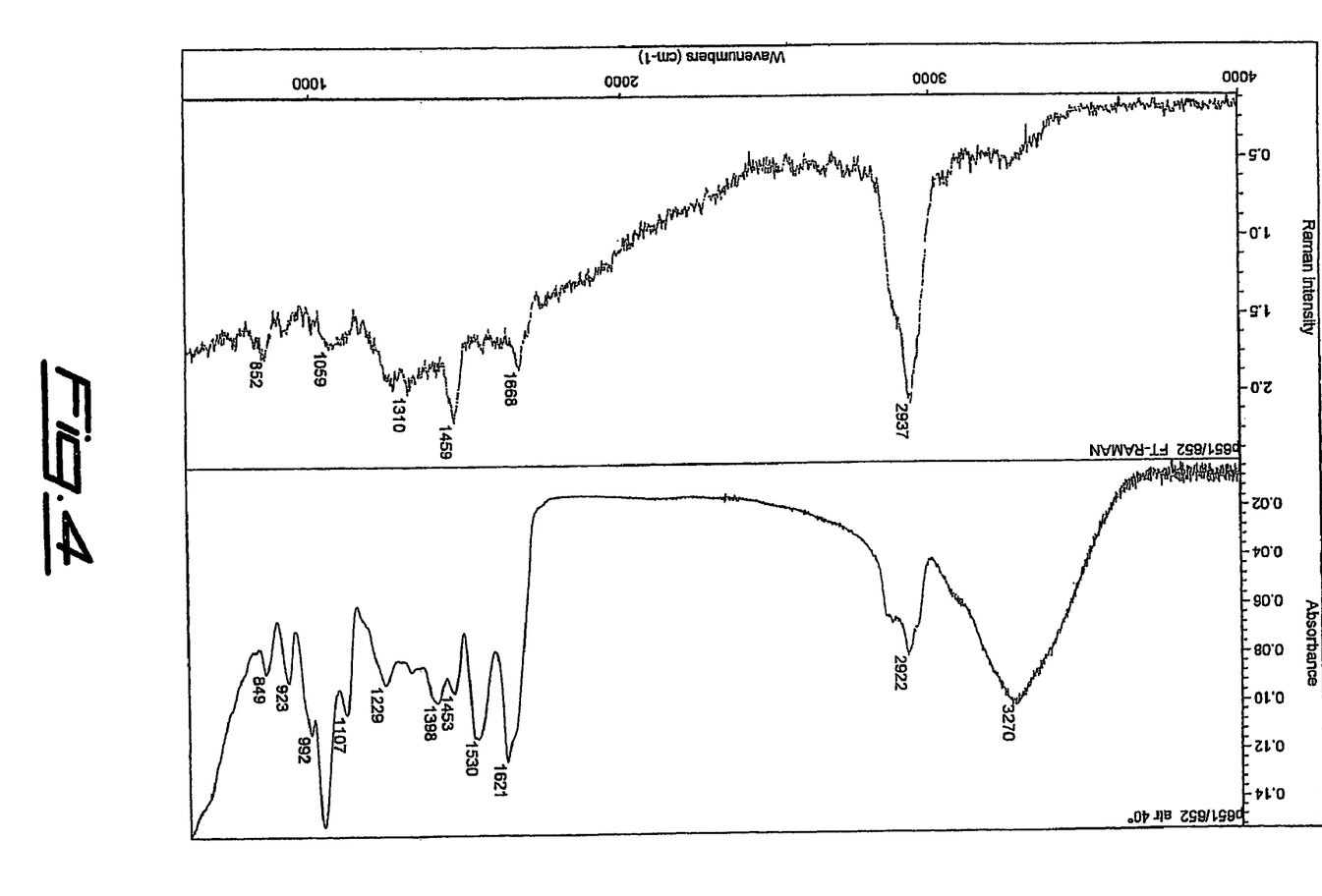
FIG. 4 shows an infrared spectrum of said sample A.

At last, on sample A an attenuated total reflectance Fourier transform infrared (ATR-FTIR) spectrometry analysis and a Raman spectroscopy analysis were carried out by using a Magna 560 Nicolet spectrophotometer, having an ATR Model 300 Spectra Tech cell. The resulting spectra relating to sample A are shown in FIG. 4.

EXAMPLE 3

The square shaped sample B (63 mm×63 mm) was cut out from a human fibrin membrane obtained according to the above-mentioned process, that was sterilized using the STERRAD method (in $H_2O_2$ at 45° C.) and stored at room temperature. As for sample A, also sample B was subjected to mechanical tensile tests and breaking strength tests, as well as to a morphological analysis at the electron microscope, after having determined the thickness of the membrane.

For sample B, the same procedure was followed using the same equipment as in the Example 2, for the thickness determination. To check the uniformity level of the considered membrane, thickness measurements were carried out in ten different points of the membrane spaced apart between them and from the edges by about 10 mm. The detected values are given as follows:

| Sample | Mean thickness (μm) | Maximum thickness (μm) | Minimum thickness (μm) |
|---|---|---|---|
| B | 47 | 56 | 14 |

Tensile Tests

The mechanical properties of sample B were evaluated according to the procedures used in Example 2.

Figure 5A:
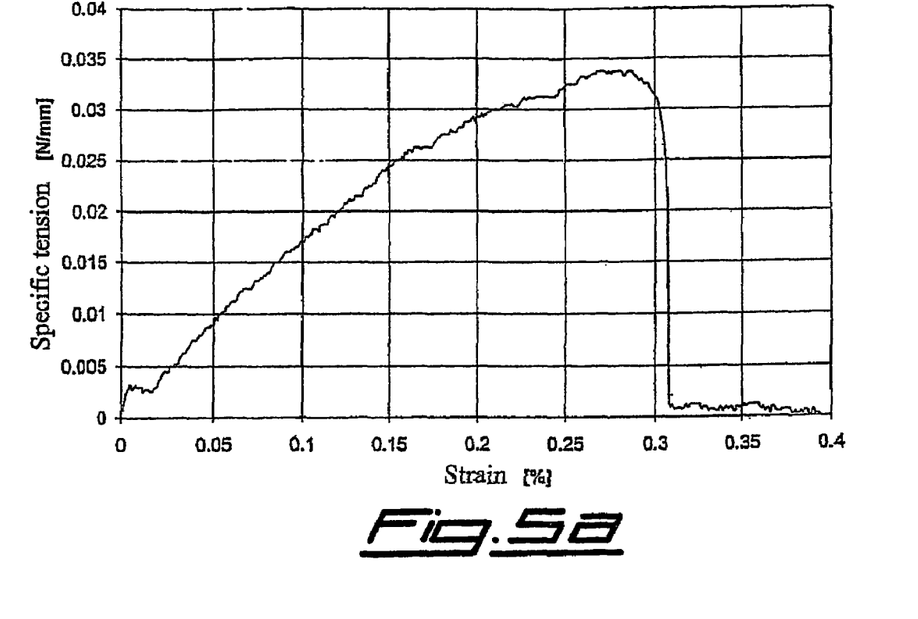
FIGS. 5a and 5b show the relationship between specific tension and strain in two specimens of a same sample B of fibrin membrane, subjected to tensile tests.
Figure 5B:
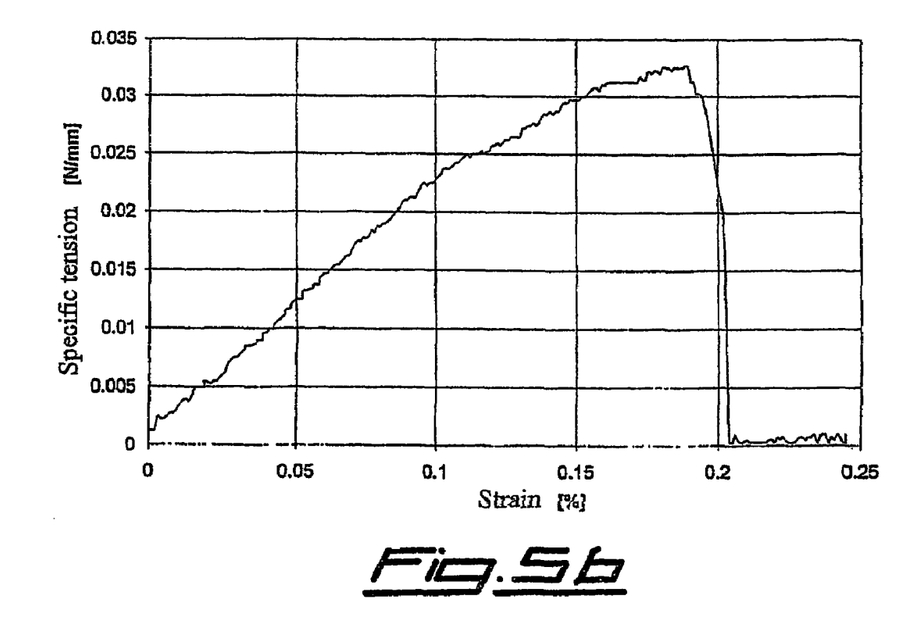

The results of such tests are represented in terms of specific tension/strain ratio in FIGS. 5a and 5b, whereas for a quantitative evaluation of properties of both test-pieces, the following data are given:

| Specimen | Thickness (μm) | Modulus of elasticity K (N/mm) | Proportionality limit $T_P$ (N/mm) | Breaking limit $T_R$ (N/mm) |
|---|---|---|---|---|
| 1 | 47 | 0.220 | 0.025 | 0.033 |
| 2 | 47 | 0.174 | 0.025 | 0.034 |

Figure 6:
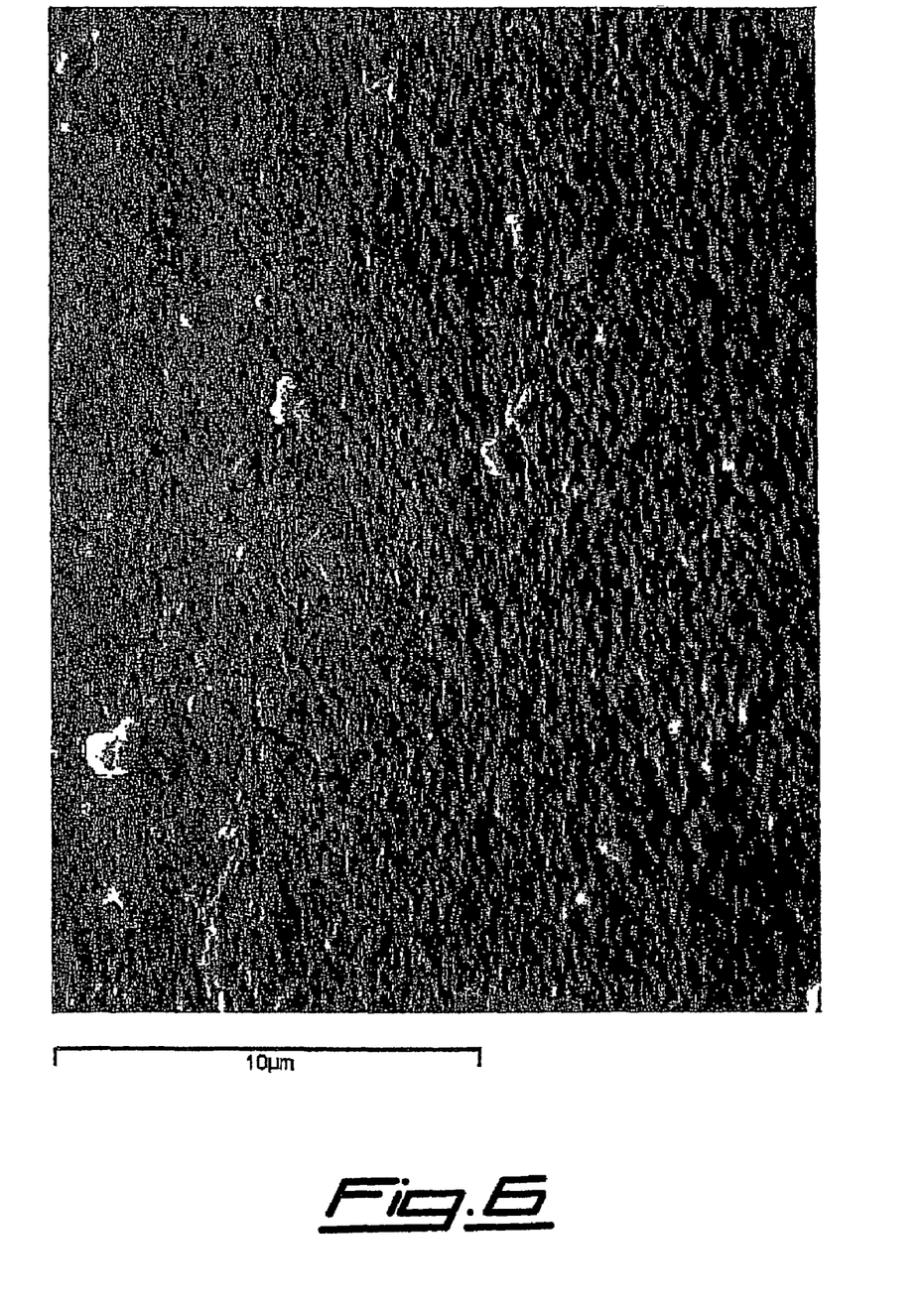
FIG. 6 shows an electron microscope image of said sample B.

In addition, sample B was observed at the electron microscope: the surface image thereof is shown in FIG. 6.

Figure 7:
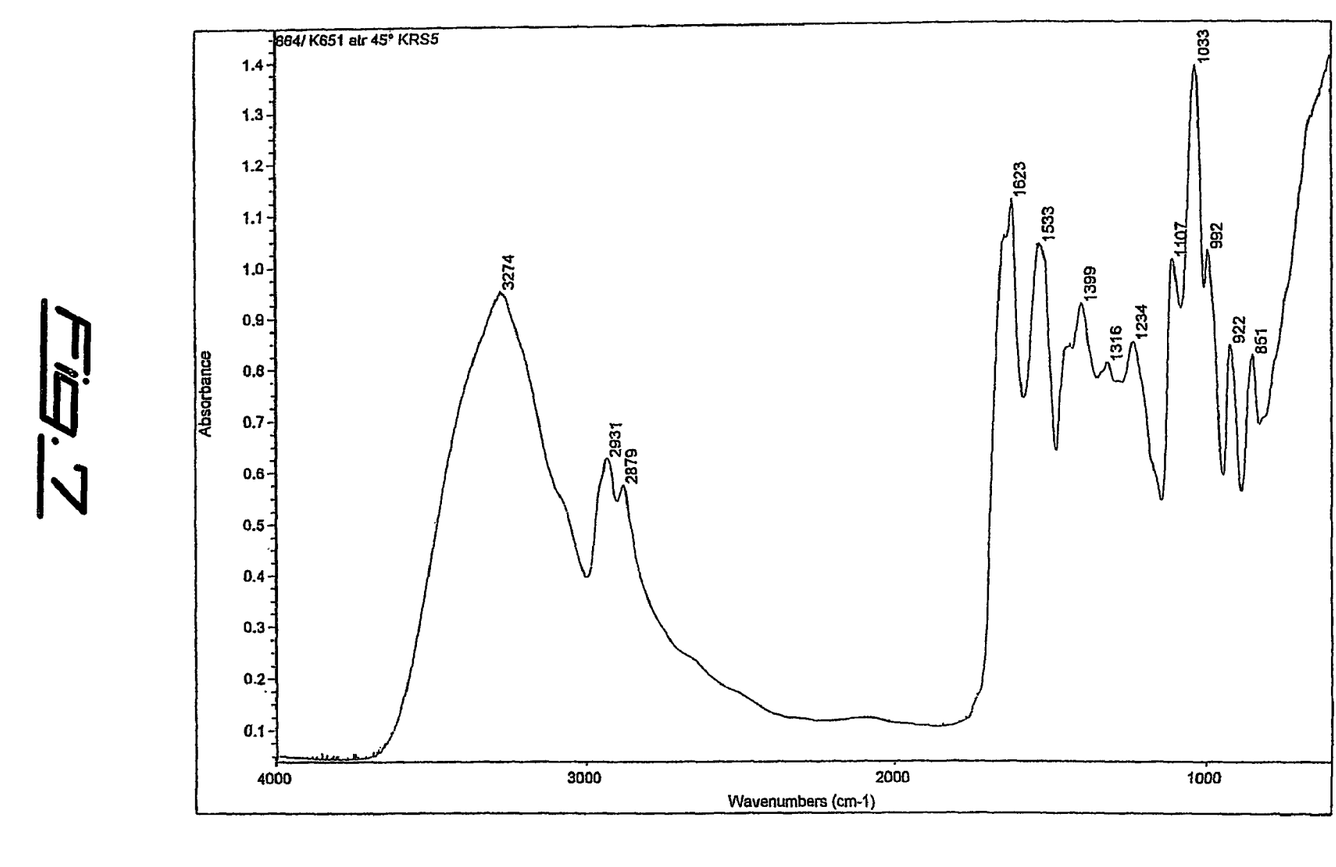
FIG. 7 shows an infrared spectrum of said sample B.

At last, on sample B an attenuated total reflectance Fourier transform infrared (ATR-FTIR) spectrometry analysis was carried out by using the same spectrophotometer as in Example 2. The resulting spectrum relating to sample B is shown in FIG. 7.

EXAMPLE 4

The rectangular shaped sample C (66 mm×128 mm) was cut out from a human fibrin membrane obtained according to the above-mentioned process, that was sterilized in autoclave at 120° C. and stored at room temperature. As for samples A and B, also sample C was subjected to mechanical tensile tests and breaking strength tests, as well as to a morphological analysis at the electron microscope, after having determined the thickness of the membrane.

For sample C, the same procedure was followed by using the same equipment as in the Example 2, for determining the thickness. To check the uniformity level of the considered membrane, thickness measurements were carried out in ten different points of the membrane spaced apart between them and from the edges by about 10 mm.

The detected values were as follows:

| Sample | Mean thickness (μm) | Maximum thickness (μm) | Minimum thickness (μm) |
|---|---|---|---|
| C | 97 | 111 | 76 |

Tensile Tests

The mechanical properties of sample C were evaluated by the same procedures used in Example 1.

Figure 8A:
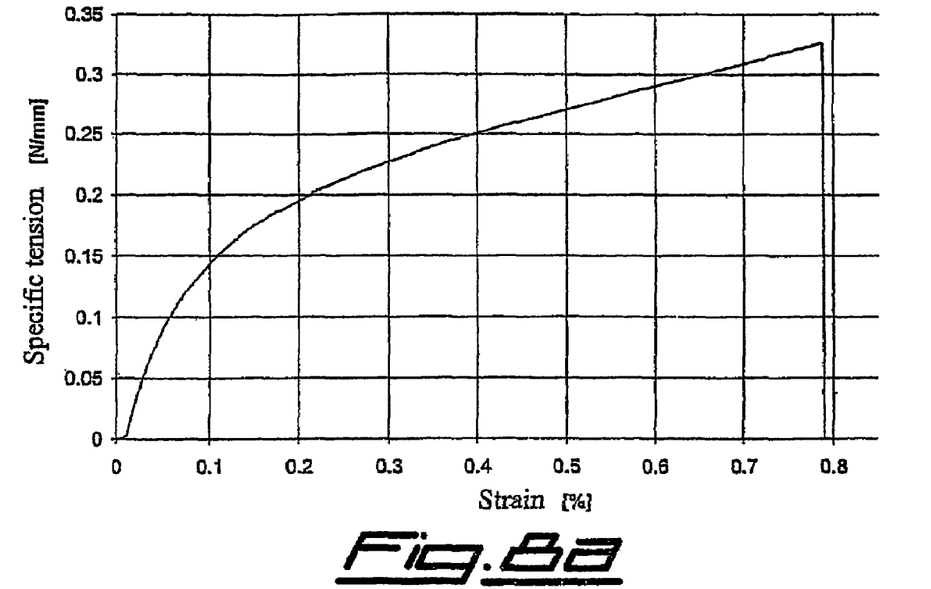
FIGS. 8a and 8b show the relationship between specific tension and strain in two specimens of a same sample C of fibrin membrane, subjected to tensile tests.
Figure 8B:
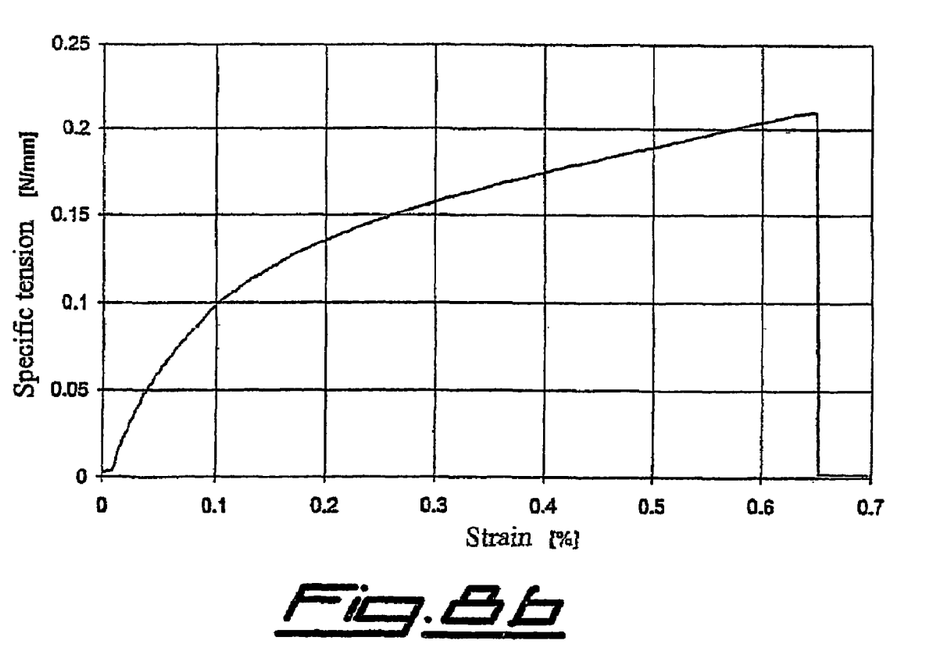

The results of such tests are represented in terms of the specific tension/strain ratio in FIGS. 8a and 8b, whereas for a quantitative evaluation of the properties of both test-pieces, the following data are given:

| Specimen | Thickness (μm) | Modulus of elasticity K (N/mm) | Proportionality limit $T_P$ (N/mm) | Breaking limit $T_R$ (N/mm) |
|---|---|---|---|---|
| 1 | 97 | 2.525 | 0.081 | 0.326 |
| 2 | 97 | 1.550 | 0.053 | 0.210 |

Figure 9:
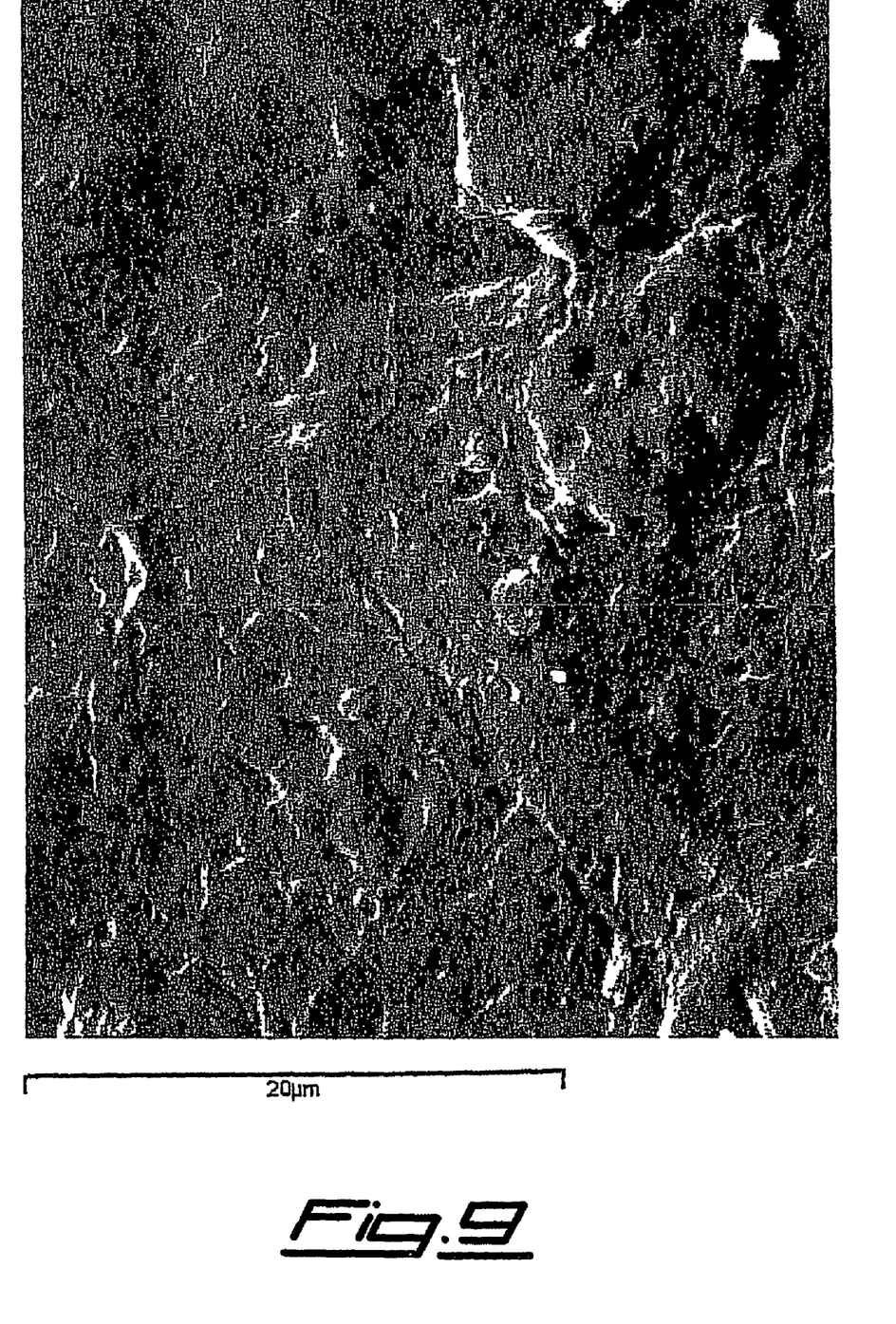
FIG. 9 shows an electron microscope image of said sample C.

In addition, sample C was studied at the electron microscope: the surface image thereof is shown in FIG. 9.

Figure 10:
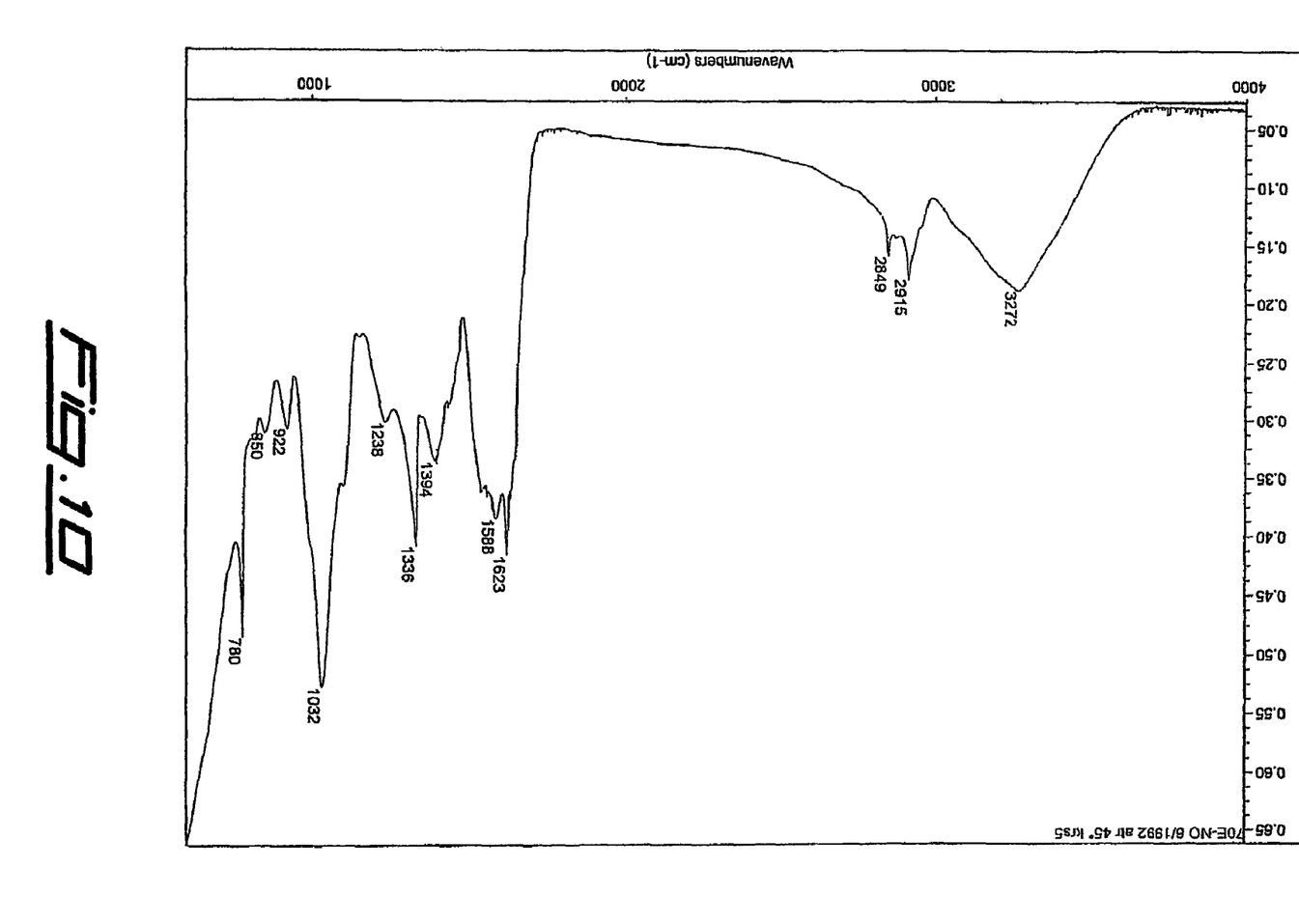
FIG. 10 shows an infrared spectrum of said sample C.

At last, on sample C an attenuated total reflectance Fourier transform infrared (ATR-FTIR) spectrometry analysis was carried out by using the same spectrophotometer as in Example 2. The resulting spectrum relating to sample C is shown in FIG. 10.

The test results resumed in the above-given tables and illustrated in the annexed drawings clearly show that by the process according to the present invention, yet starting from a discarded raw material, such as depleted blood plasma, it is possible to obtain a fibrin membrane provided with high mechanical characteristics comparable to those of membranes obtained according to prior art.

The invention claimed is:

1. A process for manufacturing a fibrin membrane, characterized in that it comprises the steps of:
    a) adding a physiological coagulating agent to blood plasma, up to gelling and clot formation;

b) removing a transudate from said blood clot by means of a physiological absorbent agent to form a membrane;

c) washing said membrane with a dehydrating and a softening agent; and d) drying and sterilizing said washed membrane.

2. The process according to claim 1, characterized in that said physiological coagulating agent is calcium chloride.

3. The process according to claim 1 or 2, characterized in that said physiological absorbent agent is an inorganic salt.

4. The process according to claim 3, characterized in that said inorganic salt is NaCl, NaHCO3 or a mixture thereof.

5. The process according to claim 1, characterized in that said softening agent is an alcohol in propane-triol.

6. The process according to claim 5, characterized in that said alcohol in propane-triol is ethanol in propane-triol.

7. A fibrin membrane, characterized in that it is obtained by the process according claim 1.

8. The fibrin membrane according to claim 7, characterized in that it shows a modulus of elasticity between 0.070 and 2.600 N/mm.

9. The fibrin membrane according to claim 7, characterized in that it shows a breaking limit between 0.030 and 0.350 N/mm.

10. The fibrin membrane according to claim 7, characterized in that it shows a proportionality limit tension/strain between 0.025 and 0.085 N/mm.

11. The fibrin membrane according to claim 7, characterized in that it is impregnated with disinfectant agents.

12. The fibrin membrane according to claim 7, characterized in that it is impregnated with drugs.

13. The fibrin membrane according to claim 7, characterized in that it is impregnated with tissue growth factors.

* * * * *